United States Patent
Bee et al.

(10) Patent No.: US 8,758,339 B2
(45) Date of Patent: *Jun. 24, 2014

(54) ANGLE INDEXER FOR MEDICAL DEVICES

(75) Inventors: David Bee, Groton, MA (US); Robert Rioux, Ashland, MA (US); Christopher J. Elliott, Hopkinton, MA (US)

(73) Assignee: Boston Scientific Scimed, Inc., Maple Grove, CA (US)

( * ) Notice: Subject to any disclaimer, the term of this patent is extended or adjusted under 35 U.S.C. 154(b) by 875 days.

This patent is subject to a terminal disclaimer.

(21) Appl. No.: 12/037,881

(22) Filed: Feb. 26, 2008

(65) Prior Publication Data

US 2008/0147059 A1    Jun. 19, 2008

Related U.S. Application Data

(60) Division of application No. 10/915,589, filed on Aug. 9, 2004, now Pat. No. 7,361,174, which is a continuation-in-part of application No. 10/317,796, filed on Dec. 11, 2002, now Pat. No. 6,926,713.

(51) Int. Cl.
*A61B 18/14* (2006.01)

(52) U.S. Cl.
USPC ............................................. 606/41

(58) Field of Classification Search
USPC .............. 606/1, 3, 27–52; 128/898
See application file for complete search history.

(56) References Cited

U.S. PATENT DOCUMENTS

| | | | | |
|---|---|---|---|---|
| 3,539,034 A | * | 11/1970 | Tafeen | 604/164.09 |
| 4,269,186 A | * | 5/1981 | Loveless et al. | 604/168.01 |
| 4,565,200 A | | 1/1986 | Cosman | |
| 5,607,392 A | * | 3/1997 | Kanner | 604/86 |
| 5,836,947 A | * | 11/1998 | Fleischman et al. | 606/47 |
| 5,855,576 A | | 1/1999 | LeVeen et al. | |
| 5,989,247 A | | 11/1999 | Chambers | |
| 6,315,777 B1 | | 11/2001 | Comben | |
| 6,622,731 B2 | | 9/2003 | Daniel et al. | |
| 6,679,874 B2 | * | 1/2004 | Miser | 606/1 |
| 6,770,070 B1 | | 8/2004 | Balbierz | |
| 6,926,713 B2 | | 8/2005 | Rioux et al. | |
| 2001/0034518 A1 | | 10/2001 | Edwards et al. | |
| 2002/0065541 A1 | | 5/2002 | Fredricks et al. | |

FOREIGN PATENT DOCUMENTS

WO        WO96/29946        10/1996

OTHER PUBLICATIONS

Office Communication dated Feb. 7, 2006 for related European Application No. 03 812 895.5-1265, Applicant: Boston Scientific Limited (4 pages).
Response to Office Communication dated Jun. 5, 2006 for related European Application No. 03 812 895.5-1265, Applicant: Boston Scientific Limited (6 pages).
Office Communication dated Apr. 25, 2007 for related European Application No. 03 812 895.5-1265, Applicant: Boston Scientific Limited (3 pages).
Response to Office Communication dated Nov. 5, 2001 in European Application No. 03812895.5, applicant: Boston Scientific Limited (11 pages).

* cited by examiner

*Primary Examiner* — Linda Dvorak
*Assistant Examiner* — Khadijeh Vahdat
(74) *Attorney, Agent, or Firm* — Kacvinsky Daisak Bluni PLLC

(57) ABSTRACT

Apparatus for positioning of a medical device in body tissue includes an angle indexer which mates in at least two positions with an index-key attached to the medical device. The indexer may be hand held or otherwise secured to a separate device, such as an introducer cannula, with the medical device being rotatable relative to the indexer.

10 Claims, 12 Drawing Sheets

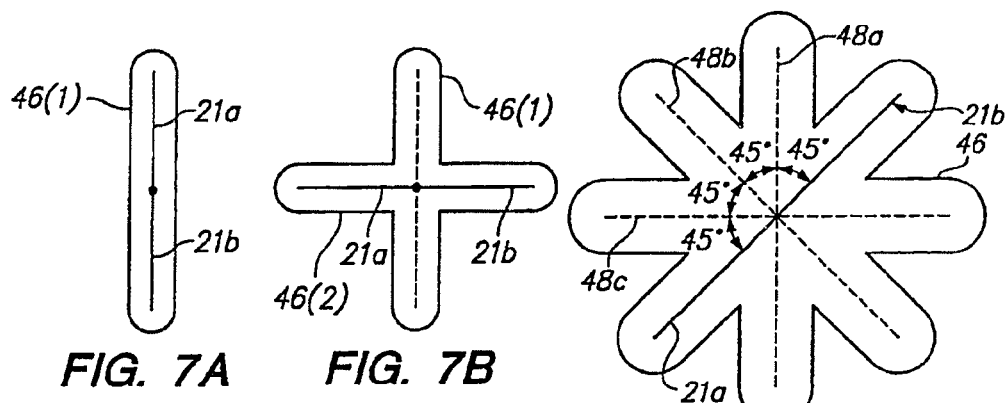
FIG. 7A  FIG. 7B  FIG. 8
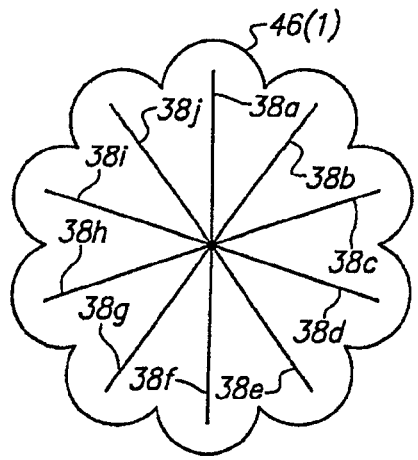
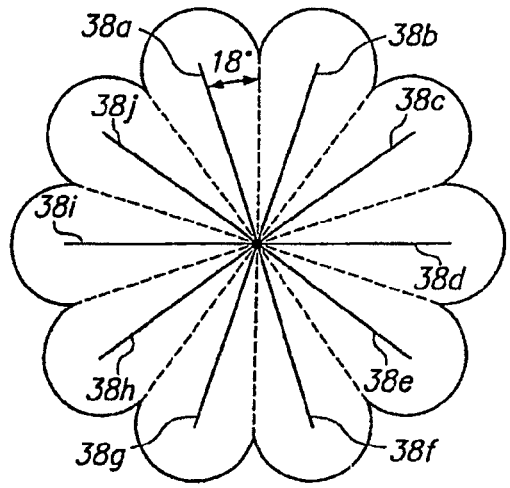
FIG. 9A  FIG. 9B
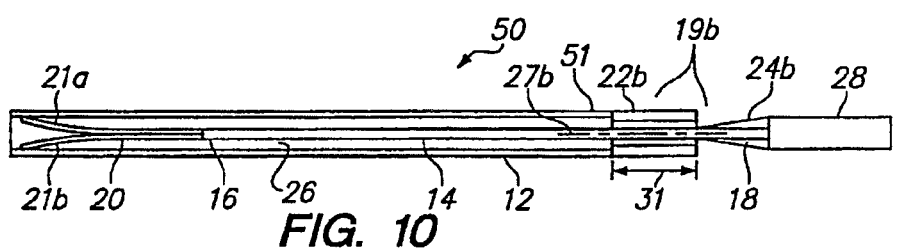
FIG. 10
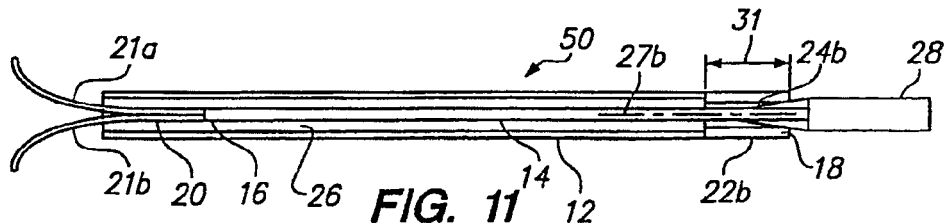
FIG. 11

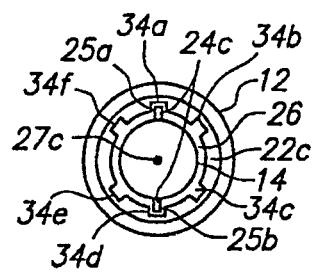
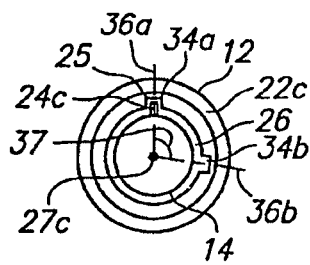
FIG. 16      FIG. 15
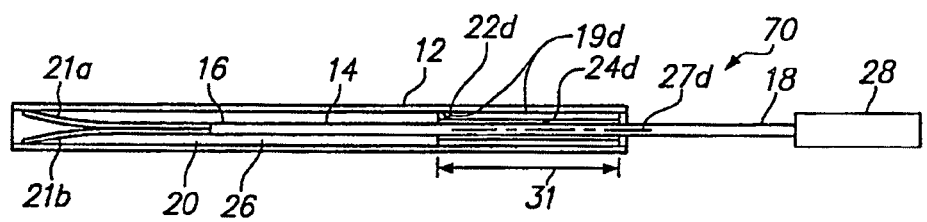
FIG. 17
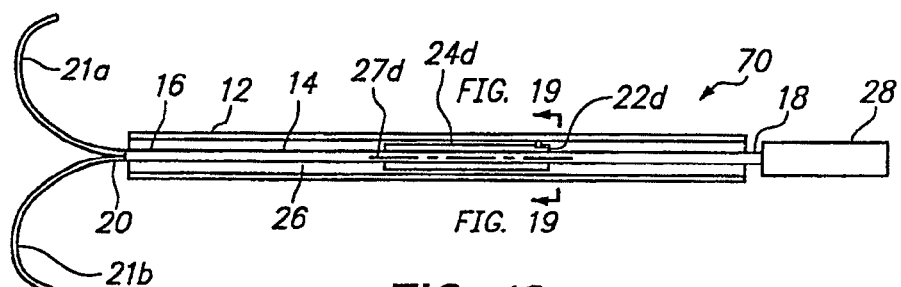
FIG. 18
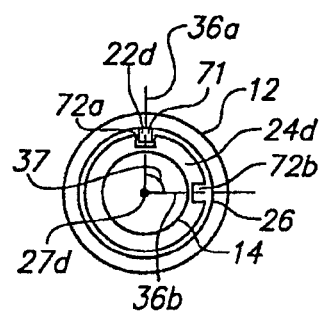
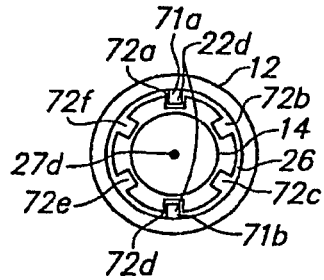
FIG. 19      FIG. 20

ANGLE INDEXER FOR MEDICAL DEVICES

RELATED APPLICATION DATA

This application is a divisional of U.S. application Ser. No. 10/915,589, filed Aug. 9, 2004, now issued as U.S. Pat. No. 7,361,174, which itself is a continuation-in-part of U.S. patent application Ser. No. 10/317,796, filed Dec. 11, 2002, now issued as U.S. Pat. No. 6,926,713, the disclosure of which are fully incorporated by reference herein.

FIELD OF INVENTION

The invention relates generally to medical devices, and more particularly, to systems for positioning medical probes in organs or cavities.

BACKGROUND

Radiofrequency ablation (RFA) involves the destruction of undesirable cells by generating heat through agitation caused by the application of alternating electrical current (radiofrequency energy) through tissue. Various RFA ablation devices have been designed to perform this treatment. For example, U.S. Pat. No. 5,855,576 describes an ablation apparatus that includes an array of wire electrodes that are deployed through a catheter. Proximal ends of the wires are connected to a RF power source (generator), with the distal ends projecting generally radially and uniformly spaced apart into a target tissue structure (e.g., a tumor) from the catheter distal end. The wire ends act as electrodes that may be energized in a monopolar or bipolar fashion to heat and necrose tissue within a defined volumetric region of target tissue. The current can flow between closely spaced energized wire electrodes or between an energized wire electrode and a larger, common electrode located remotely from the tissue to be heated. In order to assure that the target tissue is adequately treated and limit damage to adjacent healthy tissues, it is desirable that the array formed by the wires within the tissue be precisely and uniformly defined. In particular, it is generally desirable that the independent wires be evenly and symmetrically spaced-apart so that heat is generated uniformly within the desired target tissue volume. The ablation device may be used either in an open surgical setting, in laparoscopic (small incision) procedures, or in percutaneous (through the skin) interventions.

For example, FIGS. 1A to 1D show how a thermal lesion is created using the above described ablation apparatus. Using conventional imaging methods such as ultrasound, an array 2 of wires 4 is positioned strategically within the targeted area of tissue and energized with electrical current. Initially, a thermal lesion 6 begins to form at the tips of the wires 4 (FIG. 1A). The lesion 6 expands along the wires 4 back toward the center of the array 2, indicated by directional arrow 7 (FIG. 1B), then outward and between the wires 4, indicated by directional arrow 8 (FIG. 1C), until the full lesion 6 is formed (FIG. 1D).

Due to physical changes within the tissue during the ablation process, the desired thermal lesion 6 illustrated in FIG. 1D is typically difficult to achieve in a single RF application. For example, the concentration of heat adjacent the wires 4 often causes the local tissue to desiccate, thereby reducing its electrical conductivity. Also, the tissue temperature proximate the wires 4 may approach 100° C., so that water within the tissue vaporizes. As this desiccation and/or vaporization process continues, the impedance of the local tissue may rise to the point where current can no longer pass into the surrounding tissue. As such, depending on the rate of heating and how far the wire electrodes are spaced from each other, ablation devices that have multiple spreading wires may fail to create complete and uniform lesions. While wire electrodes can be repositioned to treat additional tissue, the precise movement required for this task is difficult to accomplish. Furthermore, the nature of percutaneous treatment inherently limits the ability to precisely place medical devices and sensors using traditional visual methods.

SUMMARY OF INVENTION

In accordance with a general aspect, the invention provides an angle indexing apparatus for positioning a medical device in a plurality of radial orientations. While embodiments of the invention are useful for overcoming the above-described difficulties regarding the placement and repositioning of RFA devices in a target tissue site, the invention is not so limited, but is more generally directed to placement and orientation of any medical device in body tissue.

In one embodiment, the apparatus includes an index-key configured for coupling to a medical device, and an indexer securable in a position relative to which the index-key may be rotated, wherein the index-key is adapted to mate with the indexer in at least two positions. By way of non-limiting examples, one of the indexer and index-key may have at least two keyways, with the other of the indexer and index-key having at least one key element adapted to mate with each of the at least two keyways. In one embodiment, the at least two keyways lie along two radial lines that define one or more angles equal to or less than 90°.

In embodiments of the invention, the index-key may be adapted to fit within the indexer, or vice versa. The indexer may be configured for coupling to an introducer through which the medical device is positioned in tissue. Alternately and/or additionally, the indexer may be adapted to be hand-held by an operator.

Embodiments of the invention are well-suited for certain medical devices, such as energy delivery probe having an array of spaced electrodes for performing RFA procedures in body tissue. In one such embodiment, the medical device is a RFA probe having at least two spaced electrodes that are placed in a first orientation when the index key is mated with the indexer in a first position, and in a second orientation when the index key is mated with the indexer in a second position.

In another embodiment, the medical device may be an imaging probe, a sensing (e.g., temperature) probe, or any other probe that may be selectively placed in a relative radial orientation in body tissue using the respective indexer and index-key.

In accordance with still another embodiment of the invention, a method for delivering energy to a target tissue region in a body, includes positioning an introducer in the target tissue region, the introducer having a lumen and a distal end opening, the introducer further having an indexer coupled to a proximal portion thereof; positioning an energy delivery probe through the introducer lumen so that a distal end of the energy delivery probe is positioned proximate the distal end opening of the introducer in the target tissue region, the energy delivery probe having an index-key coupled to a proximal portion thereof, the index-key adapted to mate with the indexer in at least two positions; mating the index-key and indexer in a first position, and deploying an electrode in a first orientation from the distal end of the energy delivery probe into tissue; transmitting energy from the electrode in the first orientation to tissue; withdrawing the electrode from the tissue and into the energy delivery probe; mating the index-key and indexer in a second position, and deploying the electrode in a second orientation from the distal end of the energy delivery probe into tissue; and transmitting energy from the electrode in the second orientation to tissue.

In accordance with yet another embodiment of the invention, a method of measuring temperature of a target tissue region in a body, includes positioning an introducer in the target tissue region, the introducer having a lumen and a distal end opening, the introducer further having an indexer coupled to a proximal portion thereof; positioning a temperature sensing probe through the introducer lumen so that a distal end of the temperature sensing probe is positioned proximate the distal end opening of the introducer in the target tissue region, the temperature sensing probe having an index-key coupled to a proximal portion thereof, the index-key adapted to mate with the indexer in at least two positions; mating the index-key and indexer in a first position and deploying the distal end of the temperature sensing probe in a first orientation from the introducer lumen into tissue; sensing a tissue temperature with the probe distal end in the first orientation; withdrawing the probe distal end from the tissue and into the introducer lumen; mating the index-key and indexer in a second position, and deploying the distal end of the temperature sensing probe in a second orientation from the introducer lumen into tissue; and sensing a tissue temperature with the probe distal end in the second orientation.

Other aspects and features of the invention will be evident from reading the following detailed description of the embodiments, which are intended to illustrate, and not limit, the invention.

BRIEF DESCRIPTION OF THE DRAWINGS

The drawings illustrate the design and utility of embodiments of the invention, in which similar elements are referred to by common reference numerals, and in which:

FIG. 7A is an end view of a probe assembly having two spreading wires spaced at 180°;

FIG. 7B is an end view of the probe assembly of FIG. 7A, particularly showing the position of the wires that have been rotated 90°;

FIG. 8 is an end view of the probe assembly of FIG. 7A, particularly showing the position of the wires that have been rotated 45° three times;

FIG. 9A is an end view of a probe assembly having ten spreading wires spaced at 36°;

FIG. 9B is an end view of the probe assembly of FIG. 9A, particularly showing the position of the wires that have been rotated 18°;

FIG. 10 is a side cross sectional view of a an angle indexing apparatus in accordance with another embodiment of the invention;

FIG. 11 is a side cross sectional view of the probe assembly of FIG. 10, particularly showing the wires deployed at the distal end of the cannula;

FIG. 15 is a cross sectional view of the probe assembly of FIG. 14, particularly showing the index-key mated with the indexer;

FIG. 16 is a cross sectional view of a variation of the angle indexing apparatus of FIG. 15, particularly showing the index-key having more than two adjustable positions relative to the indexer;

FIG. 17 is a side cross sectional view of a probe assembly having an angle indexing apparatus in accordance with another embodiment of the invention;

FIG. 18 is a side cross sectional view of the probe assembly of FIG. 17, particularly showing the wires deployed at the distal end of the cannula;

FIG. 19 is a cross sectional view of the probe assembly of FIG. 18, particularly showing the index-key mated with the indexer;

FIG. 20 is a cross sectional view of a variation of the angle indexing apparatus of FIG. 19, particularly showing the index-key having more than two adjustable positions relative to the indexer;

DETAILED DESCRIPTION OF THE ILLUSTRATED EMBODIMENTS

Figure 1A:
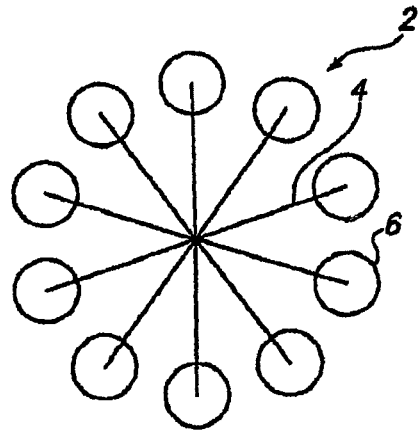
FIGS. 1A-1D shows various phases of a prior art lesion formation process using an ablation device having multiple wires.
Figure 1B:
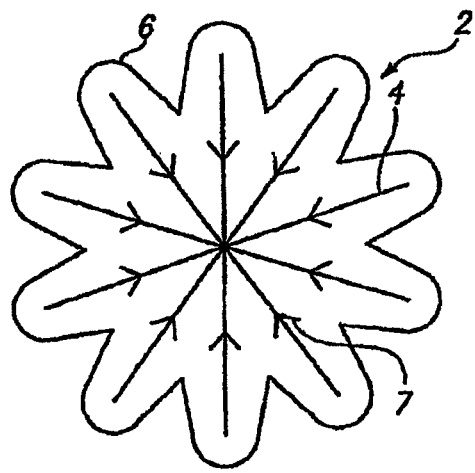
Figure 1C:
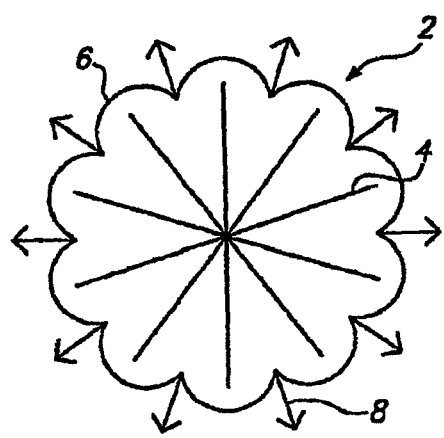
Figure 1D:
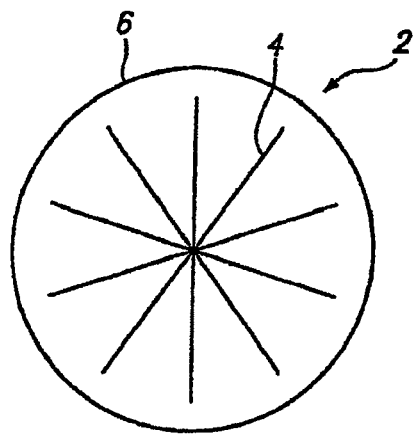

Various embodiments of the invention are described hereinafter with reference to the figures. It should be noted that the figures are not drawn to scale and that elements of similar figures structures or functions are represented by like reference numerals throughout the figures. It should also be noted that the figures are only intended to facilitate the description of specific embodiments and are not intended as an exhaustive description or as a limitation on the scope of the invention. Aspects, features, and advantages described in conjunction with a particular embodiment are not necessarily limited to that embodiment and may be practiced with other embodiments of the invention, even if not so illustrated or specifically described. Similarly, while the disclosed embodiments are primarily energy delivery probes, such as RFA probes, the invention is not so limited to such devices or uses, and may be employed for other device types and uses, such as biopsy or temperature probes.

Figure 2:
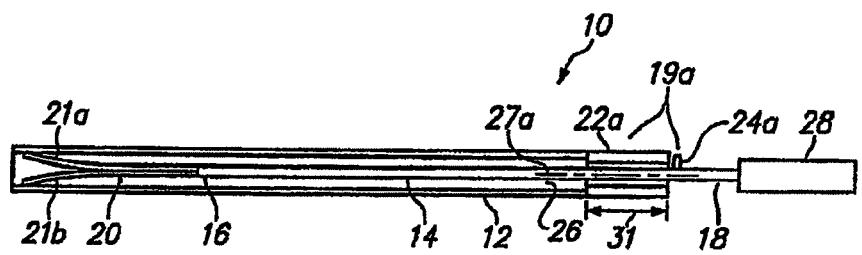
FIG. 2 is a side cross sectional view of a probe assembly that includes an angle indexing apparatus in accordance with one embodiment of the invention.

Referring to FIG. 2, a probe assembly 10 constructed in accordance with one embodiment of the invention is shown. The probe assembly 10 includes a tubular element, such as a cannula 12, an elongate member, such as a shaft 14, having a distal end 16 and a proximal end 18, an operative element 20 carried on the distal end 16 of the shaft 14, and an angle indexing apparatus 19. The angle indexing apparatus 19 includes an indexer 22a mounted to the proximal end of the cannula 12, and an index-key 24a mounted to the proximal end 18 of the shaft 14. As used in this specification, the index-key 24 refers to the component of the indexing apparatus 19 that is coupled to (and therefore, associated with) the shaft, or other part(s) of the probe assembly that carries the operative element 20. The shaft 14 is coaxially surrounded by the cannula 12 and is capable of being advanced or retracted coaxially within a lumen 26 of the cannula 12. The probe assembly 10 optionally includes a handle 28 connected to the proximal end 18 of the shaft 14. A marker (not shown) may also optionally be placed at the handle 28 or at the proximal end 18 of the shaft 14 for indicating the orientation of the shaft 14 and the operative element 20. The probe assembly 10 may also optionally include a sensor, such as a temperature sensor or an impedance sensor (not shown), carried at the distal end of the shaft 14.

The cannula 12 may be made of a variety of materials, including, but not limited to, plastics, metals, and polymers. Preferably, the cannula 12 is rigid, i.e., by being made of a stiff material, or by being reinforced with a coating or coil, to provide axial strength. The outer diameter of the cannula 12 is preferably less than ½ inch. However, other dimensions for the outer diameter of the cannula 12 may also be appropriate, depending on the particular application or clinical procedure. The cannula 12 should have an inner diameter that allows the shaft 14 to be inserted and slid within the lumen 26 of the cannula 12.

The shaft 14 is preferably rigid and is composed of a metal. However, the shaft 14 may also be made of other materials, including, but not limited to plastics, nitinol, titanium, methacrylates, and alloys. The shaft 14 preferably has a circular cross section. Alternatively, the shaft 14 may have other cross sectional shapes, such as square, rectangle, or customized shapes.

In the embodiment shown in FIG. 2, the operative element 20 includes a plurality of electrically conductive wires 21 that are secured at a proximal end, forming an electrode array. In particular, the proximal ends of the wires 21a, 21b are preferably secured to the distal end 16 of the shaft 14, e.g., by welding, brazing, glue, screws, or other mechanical connections. If the shaft 14 has a lumen (not shown) extending between the distal end 16 and the proximal end 18 of the shaft 14, conductive wires for supplying energy to the wires 21a, 21b can be housed within the lumen. Alternatively, if the shaft 14 has a solid cross section, the conductive wires for supplying energy to the wires 21a, 21b can be housed within the lumen 26 of the cannula 12 and outside the shaft 14.

Figure 3:
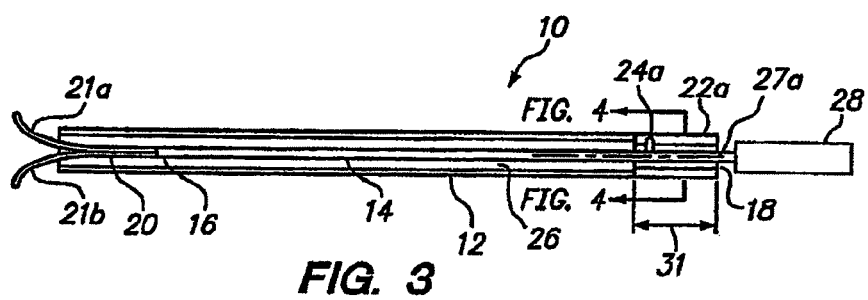
FIG. 3 is a side cross sectional view of the probe assembly of FIG. 2, particularly showing the wires deployed at the distal end of the cannula.

As shown in FIG. 2, the array of wires 21 is stretched into a low profile when the array of wires 21 is housed within the lumen 26 of the cannula 12. As illustrated in FIG. 3, advancing the proximal end 18 of the shaft 14, or the handle 28 if one is provided, pushes the wires 21a, 21b out of the lumen 26 of the cannula 12. When the wires are unconfined by the cannula 12, they assume a relaxed expanded configuration. FIG. 3 shows that a two-wire array is formed with each wire 21a, 21b arching in a general "U" shape and with each wire substantially uniformly separated. Alternatively, each wire 21a, 21b may have other shapes, such as a "J" shape, and the array may have just one wire or more than two wires. The wires 21 are preferably formed of spring wire or other material which will retain memory. During use of the probe assembly 10, the wires 21 are deployed into a target tissue, and deliver ablation energy to the tissue to create a lesion.

The indexer 22a is preferably made of plastic or polymer, but can also be made of other materials, such as metals. The indexer 22a is preferably separately manufactured from the cannula 12, and is then subsequently detachably coupled to the proximal end of the cannula 12. For such purpose, a luer-type connection may be used as the securing mechanism between the indexer 22 and the proximal end of the cannula 12. Alternatively, the securing mechanism may be a friction-type connection, or a screw-type connection, as are commonly known to those skilled in the art. The indexer 22a may also be permanently secured to the proximal end of the cannula 12 by welding, brazing, glue, or other types of adhesive, depending on the materials from which the indexer 22a and the cannula 12 are made. Still another alternative is to fabricate the indexer 22a together with the cannula 12 as one single component.

Figure 4:
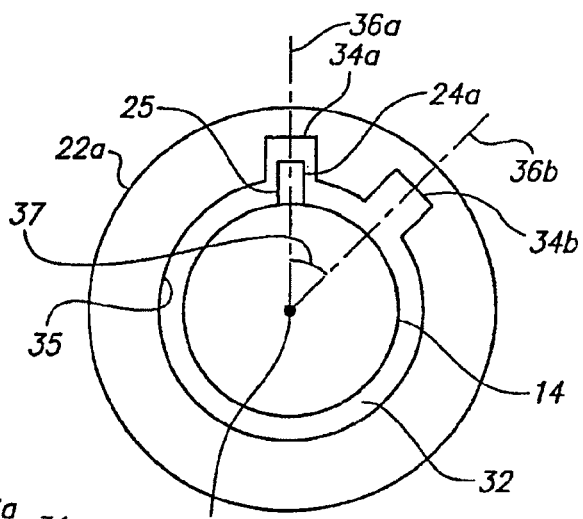
FIG. 4 is a cross sectional view of the probe assembly of FIG. 2, particularly showing the index-key mated with the indexer.

The index-key 24a is secured to the shaft 14 and includes a single key element 25 (shown in FIG. 4). The index-key 24a is preferably fabricated together with the shaft 14. Alternatively, the index-key 24a can be separately manufactured from the shaft 14, and then secured to the shaft 14 by welding, brazing, glue, or other suitable adhesives or by mechanical means. The index-key 24a can also be secured within a pre-made opening located along the body of the shaft 14.

Referring further to FIG. 4, indexer 22a preferably has a circular exterior profile. Alternatively, the indexer 22a can have other exterior profiles, such as oval or rectangular. The indexer 22a includes a bore 32 at the center through which the shaft 14 can be inserted into the cannula 12. The profile of the interior surface 35 of the indexer 22a is preferably circular, defining a circular shaped bore 32. However, the profile of the interior surface 35 of the indexer 22a can have other shapes, so long as the indexer 22a allows the shaft 14 to be inserted into the bore 32 in two positions, as will be described below.

The indexer 22a includes two keyways 34a and 34b located on the interior surface 35 of the indexer 22a. The keyways 34a and 34b are located along respective radial lines 36a and 36b, which form an angle 37 therebetween. The index-key 24a is adapted to mate with the indexer 22a, such that when the shaft 14 is inserted into the lumen 26 of the cannula 12, the key element 25 of the index-key 24a fits within one of the keyways 34a and 34b of the indexer 22a. Particularly, when the key element 25 of the index-key 24a fits within the keyway 34a of the indexer 22a, the shaft 14 is guided to slide within the lumen 26 of the cannula 12 in a first rotational orientation. When the key element 25 of the index-key 24a fits within the keyway 34b of the indexer 22a, the shaft 14 is guided to slide within the lumen 26 of the cannula 12 in a second rotational orientation that is offset from the first rotational orientation by angle 37. Accordingly, the electrode array carried at the distal end 16 of the shaft 14 can have two operative positions or orientations that correspond with the orientations of the keyways 34a and 34b of the indexer 22a. As will be described in further detail below, the designed magnitude of the angle 37 will depend on the number of wires 21.

The distance through which the index-key 24a longitudinally travels within either of the keyways 34a and 34b of the indexer 22a may vary. In the illustrated embodiment, the indexer 22a has a length 31, such that the shaft 14 is rotationally guided by the indexer 22a until the wires 21 at the distal end 16 of the shaft 14 are completely deployed. Alternatively, the shaft 14 may be rotationally guided by the indexer 22a only during the initial deployment range of the wires 21. In certain clinical situations or procedures, guiding the shaft 14 through the complete deployment range of the wires 21 may not be necessary. For example, once a portion of each of the wires 21 is deployed into a target tissue, the distal end 16 of the shaft 14 becomes rotatably secured, at least to a certain extent, by the tissue. As such, any further advancement of the shaft 14 could be guided by the tissue without the help of the angle indexing apparatus 19.

Figure 5:
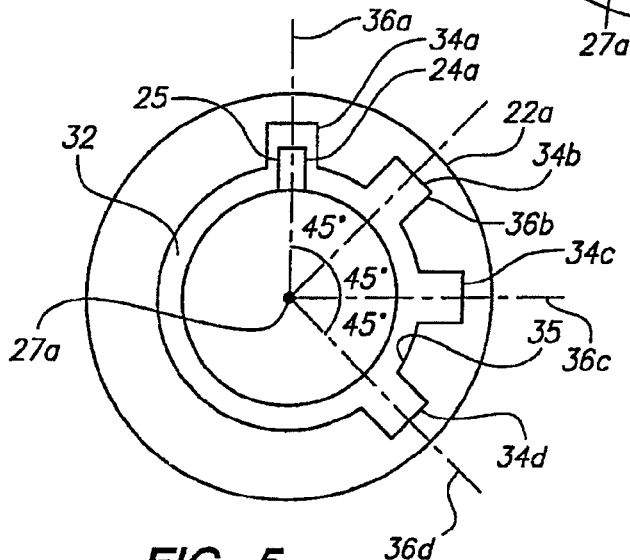
FIG. 5 is a cross sectional view of a variation of the angle indexing apparatus of FIG. 4, particularly showing the indexer having more than two keyways.

Although the previously described indexer 22a includes two keyways 34a, 34b, the number of keyways and the angle formed between the keyways may vary, depending on the particular application or clinical procedure. FIG. 5 shows a variation of the indexer 22a that includes four keyways 34a-34d located on radial lines 36a-d, respectively. The radial line 36b is 45° from the radial line 36a, the radial line 36c is 45° from the radial line 36b, and the radial line 36d is 45° from the radial line 36c. As such, each of the radial lines 36 is evenly spaced from the adjacent radial line. Alternatively, the radial lines 36 can be spaced unevenly. The shaft 14 can be guided to slide within the lumen 26 of the cannula 12 in four fixed rotational orientations by fitting the key element 25 of the index-key 24a within any one of the keyways 34a-34d.

Having just described the structure of the probe assembly 10, its operation in performing multiple ablations will now be described with reference to FIGS. 6A-6D. In this example, the indexer 22a illustrated in FIG. 4 is used, and the probe assembly 10 includes a two-wire array having wires 21a and 21b. In particular, the indexer 22a has two keyways 34a and 34b separated by an angle 37 of 90°.

Figure 6A:
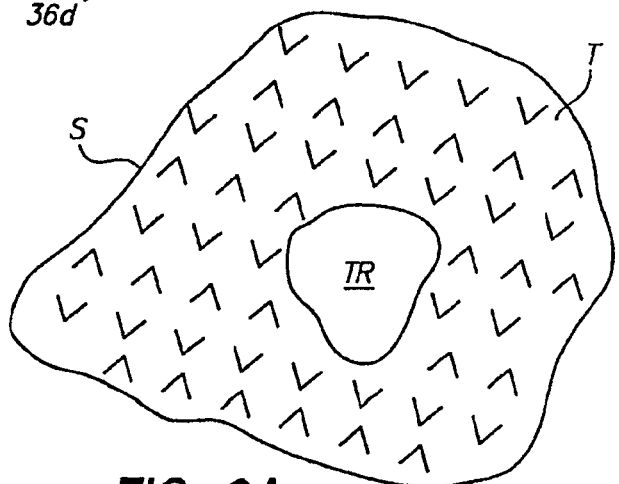
FIGS. 6A-6D illustrates cross-sectional views of one method of using the probe assembly of FIG. 2 to treat tissue.
Figure 6B:
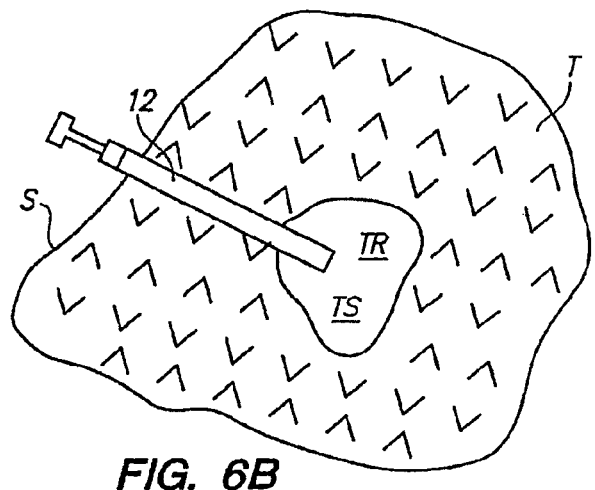

Referring now to FIGS. 6A-6D, the operation of the probe assembly 10 is described in treating a treatment region TR within a tissue located beneath the skin or an organ surface S of a patient. The tissue T prior to treatment is shown in FIG. 6A. The cannula 12 is first introduced within the treatment region TR, so that the distal end of the cannula 12 is located at the target site TS, as shown in FIG. 6B. This can be accomplished using any one of a variety of techniques. In some cases, the cannula 12 and shaft 14 may be introduced to the target site TS percutaneously directly through the patient's skin or through an open surgical incision. In this case, the cannula 12 may have a sharpened tip, e.g., in the form of a needle, to facilitate introduction to the treatment region. In such cases, it is desirable that the cannula 12 or needle be sufficiently rigid, i.e., have a sufficient column strength, so that it can be accurately advanced through tissue. In other cases, the cannula 12 may be introduced using an internal stylet that is subsequently exchanged for the shaft 14 that carries the wires 21. In this latter case, the cannula 12 can be relatively flexible, since the initial column strength will be provided by the stylet. Alternatively, a component or element may be provided for introducing the cannula 12 to the treatment region. For example, a conventional sheath and sharpened obturator (stylet) assembly can be used to initially access the target site. The assembly can be positioned under ultrasonic or other conventional imaging, with the obturator/stylet then removed to leave an access lumen through the sheath. The cannula 12 and shaft 14 can then be introduced through the sheath lumen, so that the distal end of the cannula 12 advances from the sheath into the target site TS.

Figure 6C:
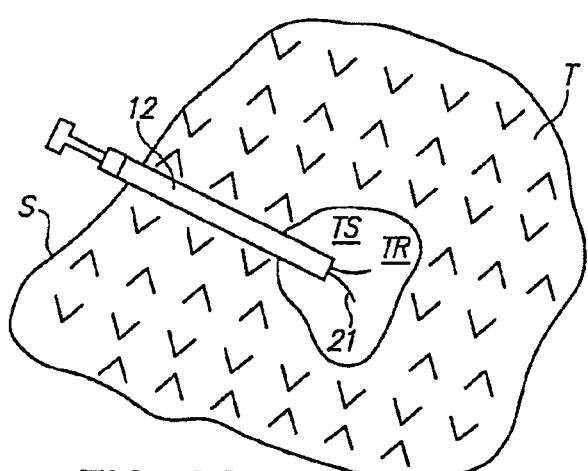
Figure 6D:
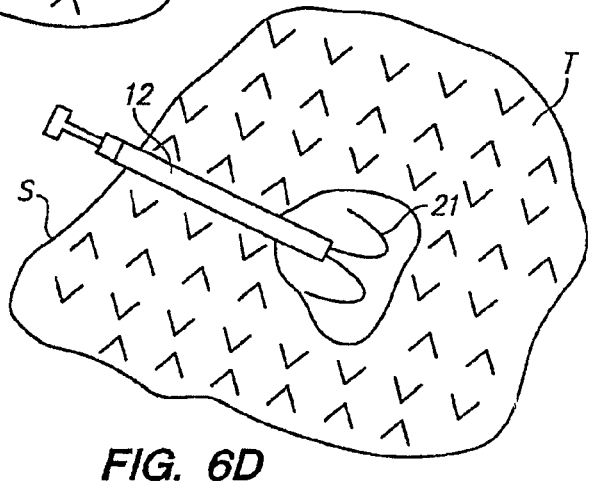

After the cannula 12 is properly placed, the shaft 14 is distally advanced until the index-key 24a is mated with the indexer 22a, thereby guiding the wires 21 to deploy radially outward from the distal end of the cannula 12, as shown in FIG. 6C. The shaft 14 will be advanced sufficiently, so that the wires 21 fully deploy in order to circumscribe substantially the entire treatment region TR, as shown in FIG. 6D.

FIG. 7A shows the wires 21a and 21b in a first deployed position when the index-key 24a is mated with the keyway 34a of the indexer 22a. While in their first deployed position, the wires 21a and 21b deliver ablation energy to create a lesion 46(1) at a target tissue. If it is desired that the wires 21a and 21b be deployed in a second position, the wires 21a and 21b are first retracted into the lumen 26 of the cannula 12 until the index-key 24a becomes disengaged with the first keyway 34a of the indexer 22a. The proximal end 18 of the shaft 14, or the handle 28 if one is provided, is then rotated until the index-key 24a is at a position at which a distal advancement of the shaft 14 would bring the index-key 24a into the second keyway 34b of the indexer 22a. The shaft 14 is then advanced distally until the index-key 24a engages with the second keyway 34b of the indexer 22a. The shaft 14 is then further advanced until the wires 21a and 21b are partially or completely deployed at the distal end of the cannula 12. Once the wires 21a and 21b are in the second deployed position, ablation energy can be delivered to the wires 21a and 21b to create a lesion 46(2) at a different region of the target tissue. FIG. 7B shows that the wires 21a and 21b are deployed in a second position that is approximately 90° from the first position, thereby forming a lesion pattern having four branches that are substantially evenly spaced.

If the indexer 22a of FIG. 5 (having four keyways 34) is used, the wires 21a and 21b can be deployed in four different positions by mating the index-key 24a within the keyways 34a-34d, respectively, of the indexer 22a. FIG. 8 shows the various rotational orientations of the wires 21a and 21b when the shaft 14 is repositioned such that the index-key 24a is mated with the four keyways 34a-d of the indexer 22a. Dash lines 48a, 48b and 48c represent the positions of the wires 21a and 21b when the index-key 24a is mated with the keyways 34a, 34b and 34c, respectively, of the indexer 22a. The solid line shown in FIG. 8 represents the fourth and current position of the wires 21a and 21b when the index-key 24a is mated with the keyway 34d of the indexer 22a. As such, by deploying the wires 21a and 21b at different positions to ablating different regions of the target tissue, a more complete and uniform lesion 46 can be created, as illustrated in FIG. 8.

In another example, the indexer 22a illustrated in FIG. 4 can be used with an ablation probe that includes a ten-wire array having wires 38a-38j spaced at substantially even intervals, i.e., 36°. In this case, the angle 37 between the keyways 34a and 34b of the indexer 22a is 18°. In the manner similarly described above, the shaft 14 is inserted within the cannula 12, index-key 24a is aligned and mated with the keyway 34a of the indexer 22a, and the shaft 14 is advanced through the cannula 12 until the wires 38a-38j are fully deployed within the target tissue (FIG. 9A). Ablation energy is then delivered to the target tissue to form a lesion 46(1). The wires 38 are then retracted into the lumen 26 of the cannula 12 until the index-key 24a becomes disengaged with the first keyway 34a of the indexer 22a. The proximal end 18 of the shaft 14, or the handle 28 if one is provided, is then rotated until the index-key 24a is at a position at which a distal advancement of the shaft 14 would bring the index-key 24a into the second keyway 34b of the indexer 22a. The shaft 14 is then advanced distally until the index-key 24a engages with the second keyway 34b of the indexer 22a. The shaft 14 is further advanced until the wires 38 are partially or completely deployed at the distal end of the cannula 12. FIG. 9B shows the first deployed position (in dashed lines) and the second deployed position of the wires 38a-j after they have been rotated 18°. Each of the wires 38a-j in the second deployed position is substantially at midpoint between the first deployed position of two of the wires 38*a-j*. Once the wires 38 are in the second deployed position, ablation energy can be delivered to the wires 38 to create a lesion 46(2) at a different region of the target tissue.

As shown in FIGS. 7-9, depending on the number of wires 21 that the device 10 contains, and the number of adjustable positions for the wires 21 desired, the angle 37 between the corresponding radial lines 36 of the keyways 34 (see FIGS. 4 and 5) can be selected, such that deployment of the wires 21 in the various respective positions could provide a substantially complete and uniform ablation coverage of the target tissue. Alternatively, the angle 37 between the radial lines 36 can be selected based on other criteria, such as the geometry or location of the target tissue.

Referring now to FIG. 10, a probe assembly 50 constructed in accordance with another embodiment of the invention is described. The probe assembly 50 is similar to the previously described probe assembly 10, however, it comprises an index-key 24*b* that includes a sleeve 52, which is capable of being secured to the shaft 14. The probe assembly 50 further includes an indexer 22*b* having an axis 27*b*, and an index-key 24*b* that is capable of mating with the indexer 22*b* in at least two positions. As shown in FIG. 11, the index-key 24*b* is mated with the indexer 22*b* when the shaft 14 is advanced to deploy the wires 21*a* and 21*b* at the distal end 16 of the shaft 14.

Figure 12:
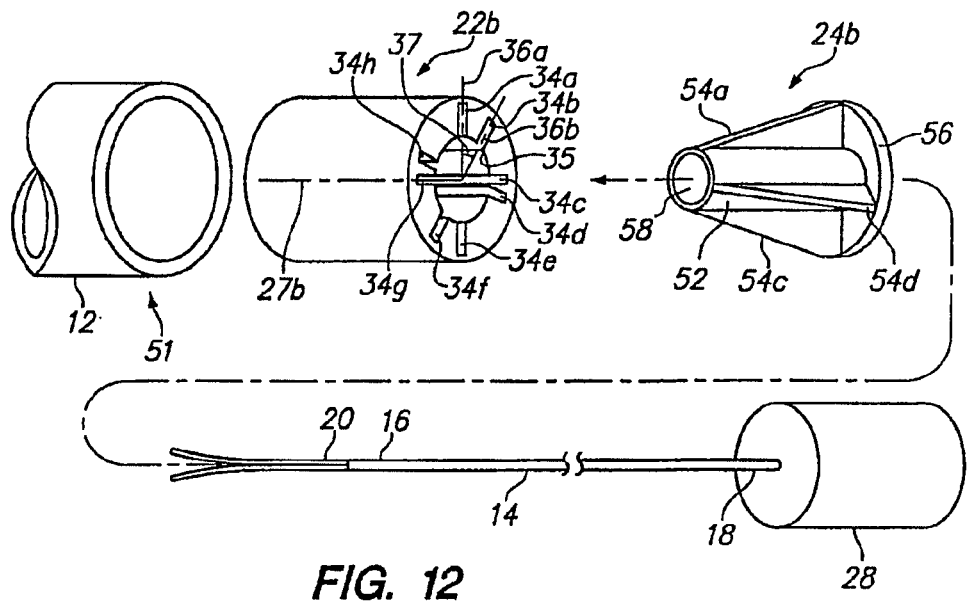
FIG. 12 is a perspective view of the probe assembly of FIG. 11, particularly showing how the indexer and index-key are coupled to the cannula and shaft, respectively.

Turning to FIG. 12, the indexer 22*b* has an interior surface 35 defining a bore 32, and a plurality of keyways 34*a-h*. Each of the keyways 34 is located along a corresponding radial line 36. As discussed previously, the indexer 22*b* can be secured to the proximal end of the cannula 12 by a variety of mechanisms, such as luer-type connection, friction-type connection, welding, glue, or screws. The sleeve 52 of the index-key 24*b* has a bore 58, and four equally spaced radially extending key elements 54 secured to the exterior surface of the sleeve 52. As illustrated in FIG. 12, the key elements 54 may be fins. Alternatively, the key elements 54 may be pins, pegs, or other projections secured to the surface of the sleeve 52. Although not required, the index-key 24*b* optionally includes a disk 56 secured to a proximal end of the sleeve 52 and the key elements 54 for the purpose of strengthening or stiffening the key elements 54.

The sleeve 52 of the index-key 24*b* is adapted to coaxially secure the shaft 14 to the index-key 24*b*. In one embodiment, the diameter of the bore 58 is made sufficiently small so that the sleeve 52 acts as a friction-type connection. Alternatively, the inner surface of the sleeve 52 and the proximal end 18 of the shaft 14 may include screw-threads, and the index-key 24*b* is then secured to the shaft 14 by screwing the shaft 14 into the threaded sleeve 58 of the index-key 24*b*. As a further alternative, the bore 58 may have a diameter that is slightly larger than the diameter of the shaft 14, and the index-key 24*b* is then secured to the shaft 14 by bonding the interior surface of the sleeve 52 to the proximal end 18 of the shaft 14. The optional proximal disk 56 can then be secured to the distal face of the handle 28 by using glue or other appropriate adhesives. It should be noted that regardless of the type of connection used to secure the index-key 24*b* to the shaft 14, the index-key 24*b* should be rigidly secured to the shaft 14 so that the index-key 24*b* cannot coaxially rotate relative to the shaft 14. An advantage of using the index-key 24*b* shown in FIG. 12 is that the index-key 24*b* can readily be used with existing devices without the need of modifying the devices.

As illustrated in FIG. 12, the four key elements 54*a-d* (key element 54*b* not shown) of the index-key 24*b* are adapted to respectively fit within the keyways 34*a*, 34*c*, 34*e*, and 34*g* of the indexer 22*b*, while guiding the shaft 14 to slide within the lumen 26 of the cannula 12 in one orientation. The key elements 54*a-d* are adapted to respectively fit within the keyways 34*b*, 34*d*, 34*f*, and 34*h* of the indexer 22*b*, while guiding the shaft 14 to slide within the lumen 26 of the cannula 12 in a second orientation. As discussed previously, the number of key elements 54 and keyways 34 may vary. Furthermore, the indexer 22*b* may have a sufficient number of keyways 34 such that it allows the shaft 14 to be operated relative to the cannula 12 in more than two orientations.

Figure 13:
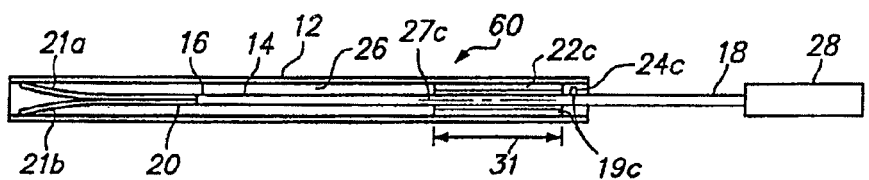
FIG. 13 is a side cross sectional view of a probe assembly having an angle indexing apparatus in accordance with another embodiment of the invention.
Figure 14:
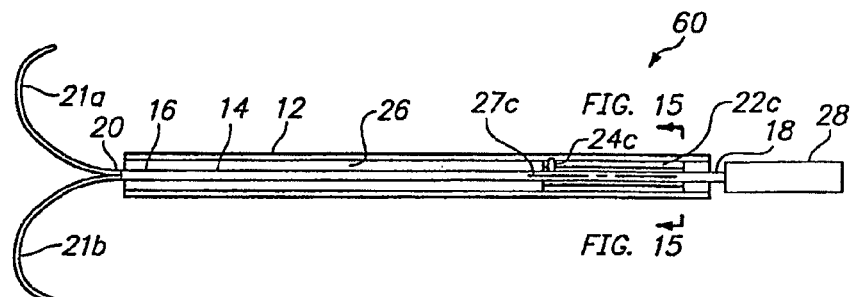
FIG. 14 is a side cross sectional view of the probe assembly of FIG. 13, particularly showing the wires deployed at the distal end of the cannula.

In all of the previously described embodiments, the indexer 22 is secured or configured to be secured to the proximal end of the cannula 12. However, the indexer 22 can also be secured to other part(s) of the cannula 12. Referring now to FIGS. 13-15, a probe assembly 60 constructed in accordance with still another embodiment of the invention is described. The probe assembly 60 is similar to the previously described probe assembly 10, with the exception that the indexer 22 is secured within the lumen 26 of the cannula 12. In the illustrated embodiment, the indexer 22*c* is secured within the proximal end of the cannula, but can be secured within the distal end or anywhere along the cannula. The indexer 22*c* is preferably secured to the cannula 12 by a friction-type connection. Alternatively, the indexer 22*c* may be detachably secured to the cannula 12 by a screw connection, or permanently secured to the cannula 12 by welding, brazing, glue, or other suitable adhesive.

Referring specifically, to FIG. 15, the index-key 24*c* has a single key element 25, and is configured to mate with the indexer 22*c* when the shaft 14 is advanced to deploy the wires 21*a* and 21*b* (FIG. 14). The indexer 22*c* has two keyways 34*a* and 34*b* for mating with the index-key 24*c*, so that the shaft 14 can be guided to slide within the lumen 26 of the cannula 12 in one orientation when the key element 25 of the index-key 24*c* is fitted within the first keyway 34*a*, and in a second orientation when the key element 25 of the index-key 24*c* is fitted within the second keyway 34*b*. Each of the keyways 34 lies along a corresponding radial line 36.

As discussed previously, the number and location of the keyways 34 may vary. The number of key elements 25 of the index-key 24*c* may also vary. For example, FIG. 16 shows a variation of the indexer 22*c* and index-key 24*c*. The indexer 22*c* includes six keyways 34*a-f*, and the index-key 24*c* has two key elements 25*a* and 25*b*. The key elements 25*a* and 25*b* are adapted to mate with two of the keyways 34*a-f* when the shaft 14 is being guided to slide within the lumen 26 of the cannula 12 in one orientation. In particular, FIG. 16 shows that the key elements 25*a* and 25*b* are respectively fitted within the keyways 34*a* and 34*d* of the indexer 22*c*. If it is desired to deploy the wires 21*a* and 21*b* in a second position, the shaft 14 is then retracted and rotated such that the keys 25*a* and 25*b* fit within the keyways 34*b* and 34*e*, respectively, of the indexer 22*c*. If it is desired to deploy the wires 21*a* and 21*b* in a third position, such can be accomplished by respectively fitting the keys 25*a* and 25*b* within the keyways 34*c* and 34*f* of the indexer 22*c*. The number of deployed positions for the wires 21 depends on the number of keys 25 and the number of keyways 34. FIG. 16 shows that the key 25*a* is located at 180° from the key 25*b*. Alternatively, the key 25*a* and the key 25*b* may be located from each other at a different angle.

In the previously discussed examples, it is the indexer 22 that includes the keyways 34, and it is the index-key 24 that includes the key(s) 25. However, the indexer 22 is not limited to having keyways and the index-key 24 is not limited to having key elements, so long as the index-key 24 is capable of mating with the indexer 22. Referring now to FIGS. 17-19, a probe assembly 70 constructed in accordance with yet another embodiment of the invention is described. The probe assembly 70 is similar to the previously described probe assembly 10, with the exception that the indexer 22 has key element(s) instead of keyways, and the index-key 24 has keyways instead of key element(s).

In particular, the probe assembly 70 includes an indexer 22d having one key element 71, and an index-key 24d having two keyways 72a and 72b. The key element 71 of the indexer 22d is preferably a projection, such as a pin, a peg, or a fin, that is secured to, or manufactured as a single unit with, an interior surface of the cannula 12. The index-key 24d has a tubular shape and an axis 27d, and is secured to the proximal end 18 of the shaft 14. Alternatively, the index-key 24d may be secured to the distal end 16 or anywhere along the shaft 14. The keyways 72 of the index-key 24d are located at an interior surface of the index-key 24d. The index-key 24d is configured to mate with the indexer 22d when the shaft 14 is advanced to deploy the wires 21a and 21b (FIG. 18). As shown in FIG. 19, the keyways 72a and 72b lie along corresponding radial lines 36a and 36b, which define an angle 37. The shaft 14 can be guided to slide within the lumen 26 of the cannula 12 in one orientation when the first keyway 72a of the index-key 24d is mated with the key element 71 of the indexer 22d, and in a second orientation when the second keyway 72b is mated with the key element 71 of the indexer 22d.

Although the illustrated embodiment of FIG. 19 shows that the index-key 24d includes two keyways 72 and the indexer 22d includes one key element 71, the number of keyways and key elements and the angle formed between the keyways may vary, depending on the particular application or clinical procedure. For example, FIG. 20 shows a variation of the indexer 22d and the index-key 24d. The indexer 22d includes two projections 71a and 71b, and the index-key 24d includes six keyways 72a-f. As FIG. 20 shows, the projections 71a and 71b of the indexer 22d fits within the keyways 72a and 72d of the index-key 24d when the shaft 14 is guided to slide within the cannula 12 in a first orientation, thereby deploying the wires 21a and 21b in a first position. If it is desired to deploy the wires 21a and 21b in a second position, the shaft 14 is first retracted. The shaft 14 is then rotated and advanced such that the projections 71a and 71b of the indexer 22d fit within the keyways 72b and 72e (or 72c and 72f of the index-key 24d, thereby, deploying the wires 21a and 21b in a second position.

Figure 21:
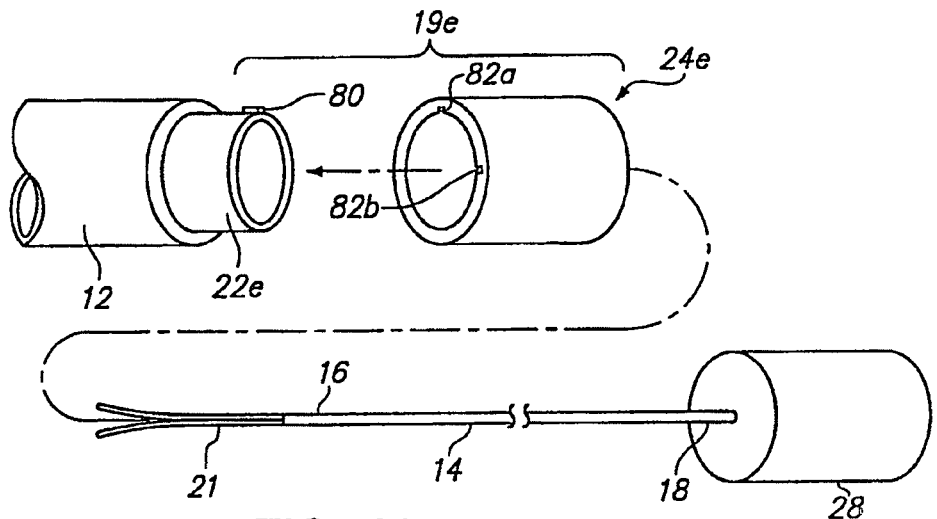
FIG. 21 is a perspective view of another variation of the angle indexing apparatus, particularly showing the indexer configured to fit within the index-key.

In all the examples discussed previously, the index-key 24 is mated within the indexer 22. The indexer 22, however, can instead be mated within the index-key 24. Referring now to FIG. 21, a probe assembly 80 constructed in accordance with still another preferred embodiment of the inventions is described. The probe assembly 80 is similar to the previously described probe assembly 70, with the exception that the indexer 22 is configured to fit within the index-key 24.

In particular, the probe assembly 80 includes an indexer 22e having one key element 81, and an index-key 24e having two keyways 82a and 82b. The key element 81 of the indexer 22e is preferably a projection, such as a pin, a peg, or a fin, that is secured to, or manufactured as a single unit with, an exterior surface of the cannula 12. The index-key 24e has a tubular shape and an axis 27d, and is secured to the proximal end 18 of the shaft 14. The keyways 82 of the index-key 24e are located at an interior surface of the index-key 24e. The key element 81 of the indexer 22e is configured to fit within one of the keyways 82 of the index-key 24e when the index-key 24e is slid to fit around the indexer 22e.

Figure 24A:
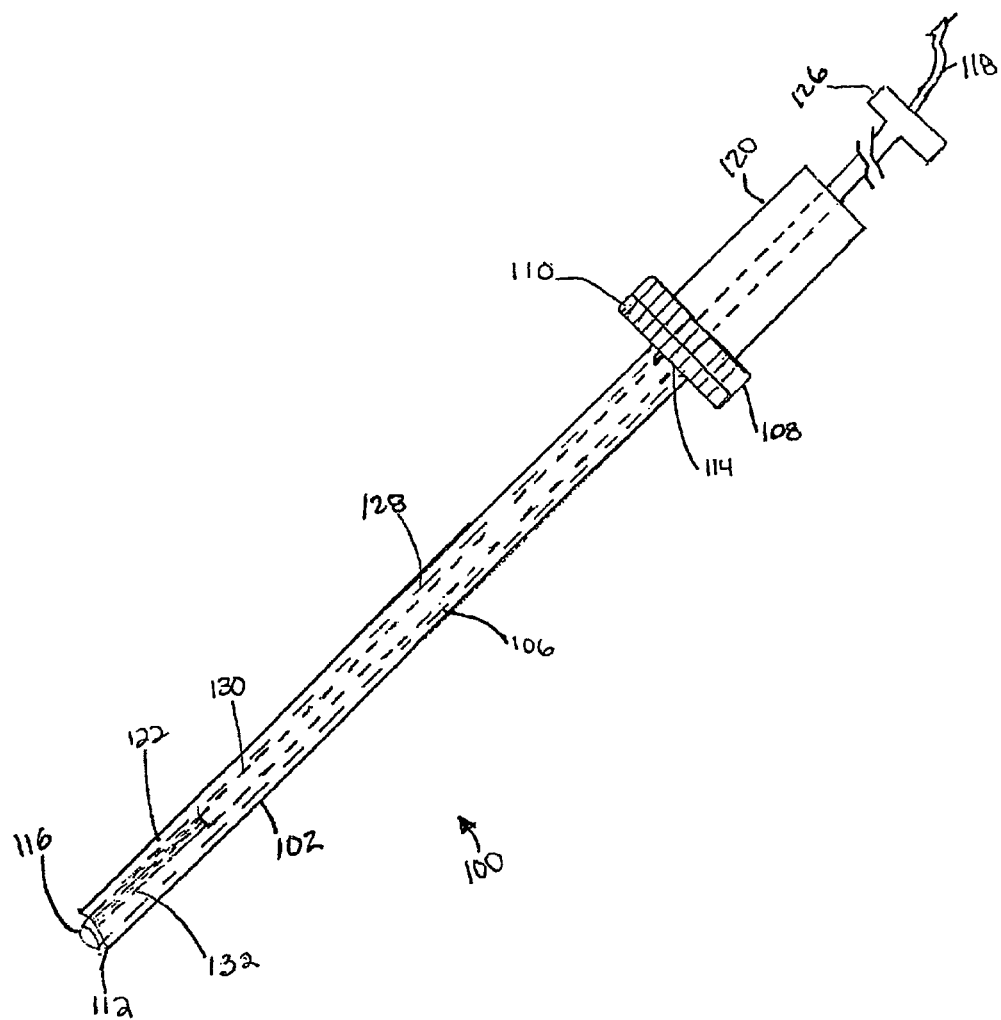
FIGS. 24A-B are side views of an energy delivery probe assembly that includes an angle indexing apparatus in accordance with an embodiment of the invention.

FIG. 24A illustrates is an energy delivery probe assembly 100 in accordance with still another embodiment of the invention. The assembly 100 generally comprises an introducer cannula 102 configured to be inserted in a conventional fashion into solid body tissue or a body cavity. An indexer 110 is attached around the periphery of the cannula 102 for positioning an energy delivery probe 106 in the body tissue or body cavity using an index key 108 attached to a handle 120 of the energy delivery probe 106. The cannula 102 is an elongated member having a distal opening 112, a proximal end 114, and an axial lumen 122 sized to allow the energy delivery probe 106 to pass through it.

The energy delivery probe 106 comprises an elongated tubular housing 128 having a distal end opening 116. Positioned within the housing 128 is a pusher 130. An array of flexible, flat wire electrodes 132 having tissue piercing ends is attached to a distal end of the pusher 130. The probe handle 120 is attached to a proximal end of the housing 128, and has a proximal end bore to allow a plunger 126 attached to the pusher 130 to be moved in and out of the handle 120. In particular, linear movement of the plunger 126 relative to the handle 120 causes a corresponding linear movement of the electrodes 132 relative to the housing 128 (and cannula 102), such that the electrodes 132 may be deployed out of the distal opening 116 of the housing 128. The index key 108 is located at the distal end of the handle 120 in order to mate with the indexer 110 at a relative position in which the electrodes 132 are completely positioned in the housing 128 when the plunger 126 is in its most proximal position relative to the handle 120, and completely deployed from the housing 128 when the plunger 126 is in its most distal position relative to the handle 120. A cable 118 is electrically connected to the electrodes 132, in order to couple the electrodes 132 to a source of RF energy (not shown).

Figure 24B:
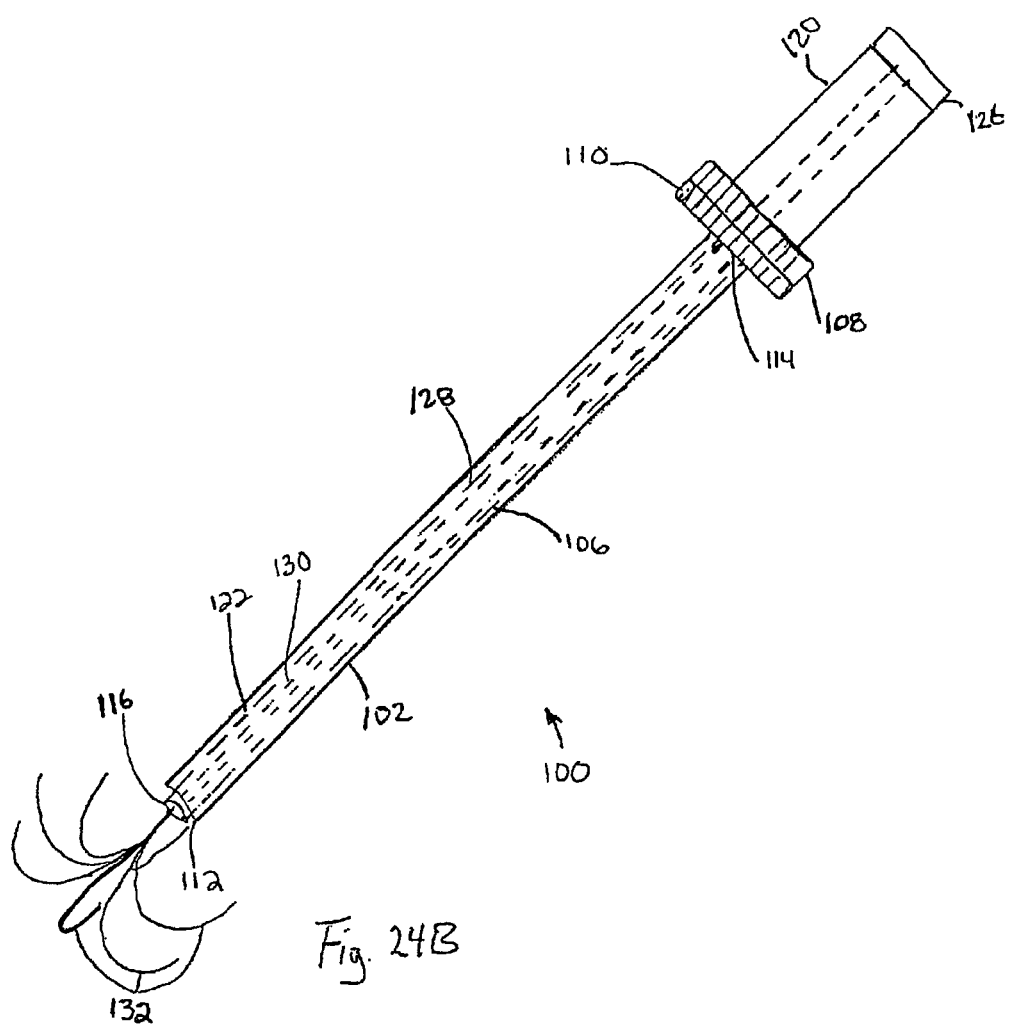

FIG. 24B shows the electrodes 132 fully deployed out of the distal housing opening 116 (and cannula opening 112), with the plunger 126 in its most distal position relative to the handle 120. This electrode deployment mechanism is similar to that embodied in the LeVeen Needle™, a commercial RFA probe sold and distributed by Boston Scientific Corporation, headquartered in Natick, Mass. In the illustrated embodiment, the deployed electrodes 132 form an inverting curve-linear pattern, i.e., mushroom or umbrella-shaped, which is also similar to the electrode array pattern of the LeVeen Needle™. However, it will be appreciated that the invention is by no means limited to such a deployment mechanism or electrode array pattern, and embodiments of the invention may be used with RFA devices having as few as a single electrode to be deployed in tissue in a direction having at least some radial component, i.e., forming an angle relative to a longitudinal axis of the probe housing 128. In particular, in embodiments of the invention, an energy delivery probe may comprise one or more electrodes deployable in a "radial" direction, which for purposes of this specification and in the following claims includes any direction having any radial component, wherein the at least one electrode may be extended in a first orientation relative to the introducer cannula when the index key is mated with the indexer in a first position, and in a second orientation relative to the introducer when the index key is mated with the indexer in a second position.

Figure 25A:
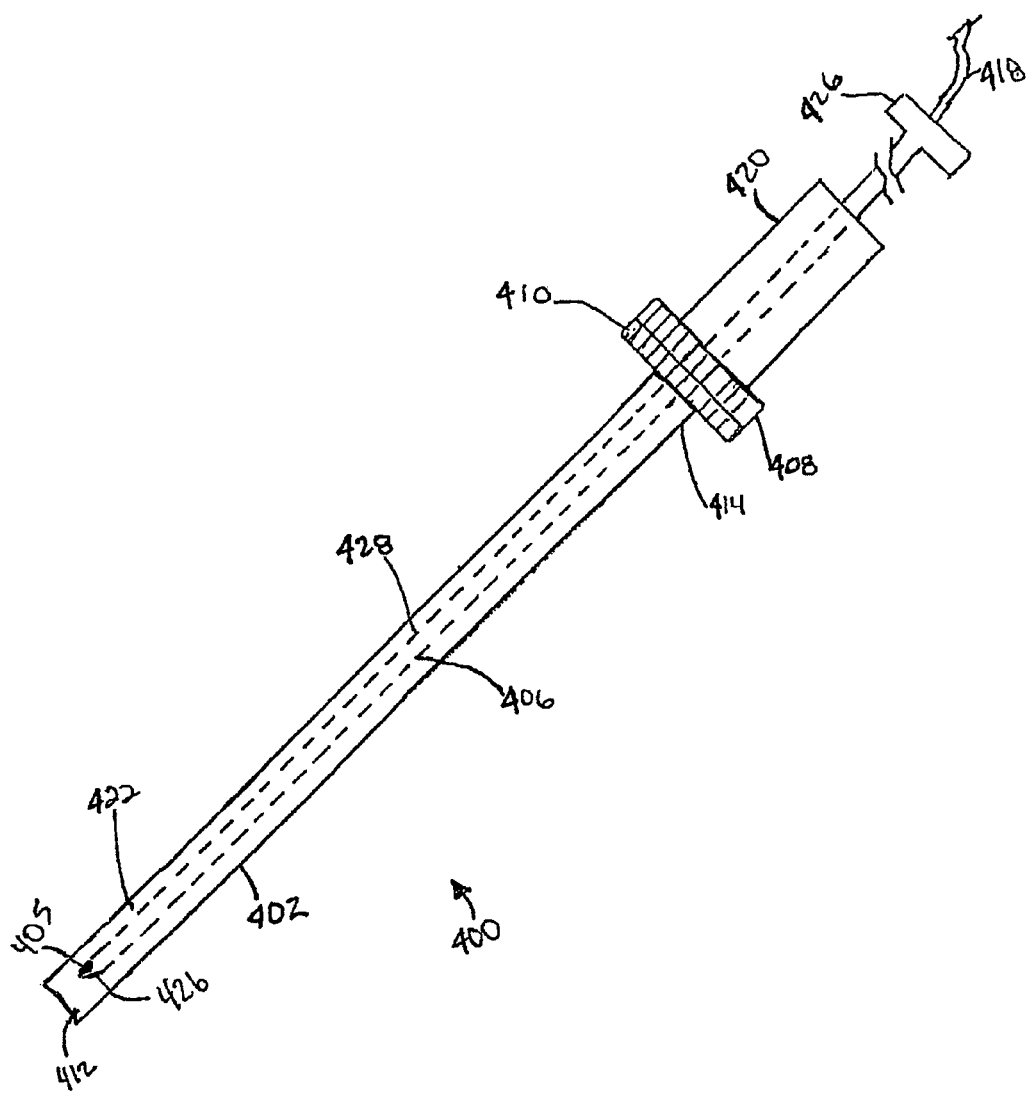
FIGS. 25A-B are side views of a temperature probe assembly that includes an angle indexing apparatus in accordance with an embodiment of the invention.

FIG. 25A illustrates a sensing probe assembly 400 in accordance with still another embodiment of the invention. The assembly 400 generally comprises an introducer cannula 402 configured to be inserted in a conventional fashion into solid body tissue or a body cavity. An indexer 410 is attached around the periphery of the cannula 402 for positioning a sensing probe 406 in the body tissue or body cavity using an index key 408 attached to a handle 420 of the sensing probe 406. The cannula 402 is an elongated member having a distal end opening 412, a proximal end 414, and an axial lumen 422 sized to allow the sensing probe 406 to pass through.

The sensing probe 406 comprises an elongated pusher member (e.g., a hypo-tube) 428 carrying a sensing element 405, such as a thermocouple for sensing temperature, or a transducer for sensing pressure, at a distal end 426 of the pusher member 428. The sensing probe handle 420 is coupled to a proximal end of the pusher member 428, the handle having a proximal end bore to allow a plunger 426 attached to the pusher member 428 to be moved in and out of the handle 420. In particular, linear movement of the plunger 426 relative to the handle 420 causes a corresponding linear movement of the pusher member 428 relative to the cannula 402, such that the distal end 426 of the probe 406 may be deployed out of the distal cannula opening 412. The index key 408 is located at the distal end of the handle 420 in order to mate with the indexer 410 at a relative position in which the sensor 405 is positioned in the cannula lumen 422 when the plunger 426 is in its most proximal position relative to the handle 420, and completely deployed from the cannula lumen 422 when the plunger 426 is in its most proximal position relative to the handle 420. A cable 418 is electrically connected to the sensor 405, in order to electrically couple the sensor to circuitry (not shown) for receiving the sensed data, e.g., corresponding to a tissue temperature or pressure.

Figure 25B:
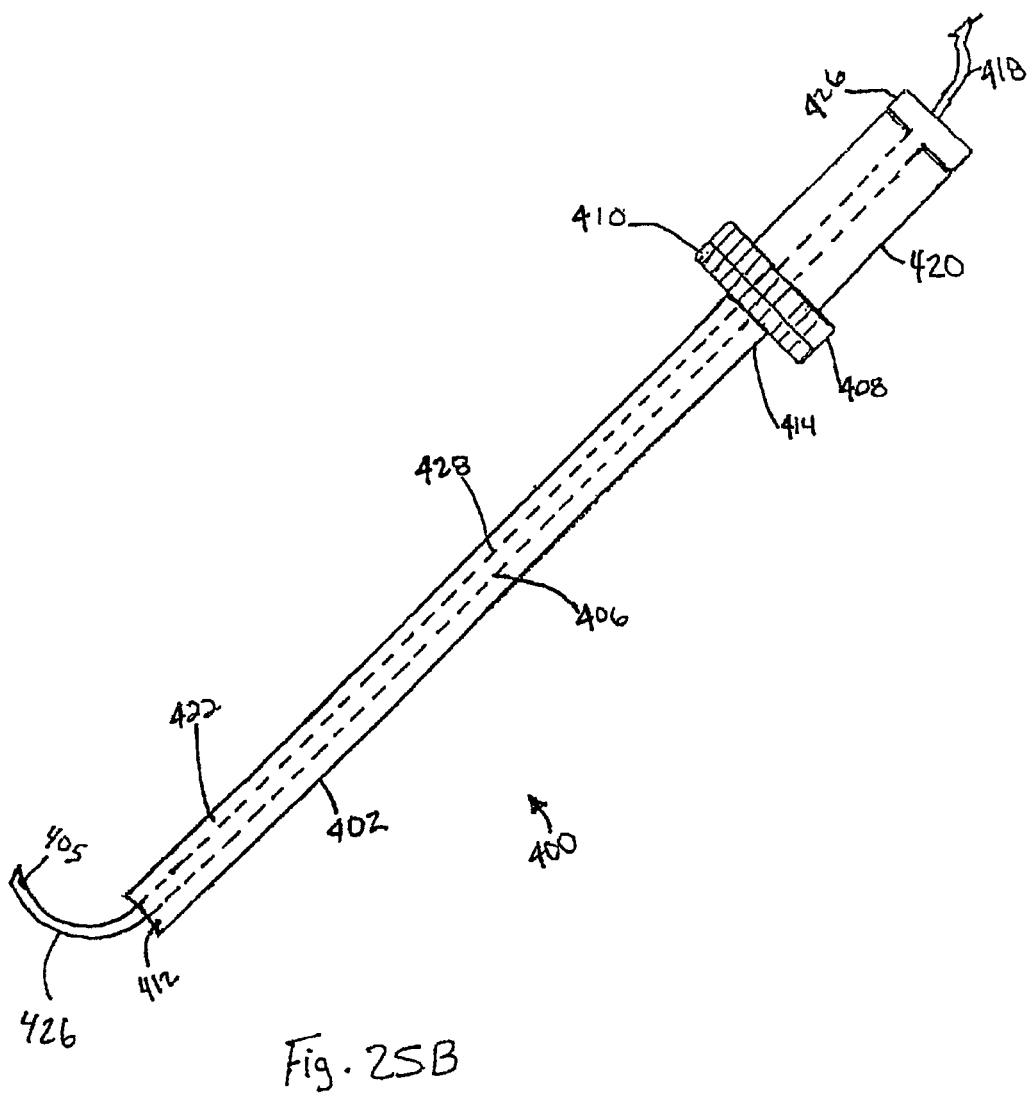

FIG. 25B shows the distal end 426 of the sensing probe 406 (and in particular sensor 405) fully deployed out of the distal cannula opening 412, with the plunger 426 in its most distal position relative to the handle 420. The distal end 426 may be provided with a tissue piercing tip in order to facilitate positioning of the sensor 405 into solid body tissue. In the illustrated embodiment, the distal end 426 of the pusher member 428 has an inverted curvilinear shape similar to the deployed electrodes 132 in FIG. 24B. Again, however, it will be appreciated that the invention is by no means limited to such a deployed shape, and embodiments of the invention may be used for positioning probes having any deployed shape that includes at least some radial component, i.e., forming an angle relative to a longitudinal axis of the cannula 402.

By way of example, the sensing probe assembly 400 may be designed to measure the temperature at a selected tissue site, e.g., for monitoring tissue temperature in conjunction with a tissue ablation procedure. The cannula 402 is inserted into body tissue by conventional means thereby providing access for the sensing probe 406, which is inserted through the cannula lumen 422 and into the body tissue, with the indexer 410 mated with the index-key 408 in a first position. The temperature sensing element 405 is deployed from the distal cannula opening 412 into the tissue site by pushing the plunger 426 forward into the handle 420. Once the sensor 405 is in place (which may be detected through conventional ultrasound means), temperature data is obtained through the cable 418. The sensor 405 is then retracted from the tissue back into the cannula lumen 422 by pulling the plunger 426 proximally relative to the handle 420. The sensing probe 406 is then rotated relative to the introducer cannula 402, and the indexer 410 is mated with the index-key 408 in a second position, thereby providing access to a second tissue site at a fixed distance from the first tissue site for the temperature sensor 405. The process may be repeated by mating the indexer and the index-keys through further orientations (or by repeating prior orientations) of the probe 406 relative to the cannula 402, until the desired tissue temperature data has been obtained.

As discussed with respect to previously described embodiments, the energy delivery probe 106 and/or sensing probe 406 may alternately be provided with an index-key that includes an axial sleeve, as depicted in FIGS. 10-12. In particular, the indexer may have has a bore of sufficient axial length to allow the index-key to act as an advancing mechanism, i.e., as the index-key is mated with the indexer, the respective electrodes or sensor are advanced into tissue or a body cavity. The indexer can be secured to the proximal end of the of the elongated member by a variety of mechanisms, such as luer-type connection, friction-type connection, welding, glue, or screws. By using an indexer and index-key pair of this type, for example, existing temperature sensing probes can be used in embodiments of the invention.

Further, an indexer can also be secured or configured to be secured to the proximal end or within the lumen of the cannula 102/402 of the probe assemblies 100/400, as depicted previously in FIGS. 13-15 for energy delivery probes assemblies. Further, one skilled in the art will recognize that the embodiments presented which specifically incorporate an energy delivery or RFA ablation probe may be adaptable for use with a sensing probe.

Figure 22:
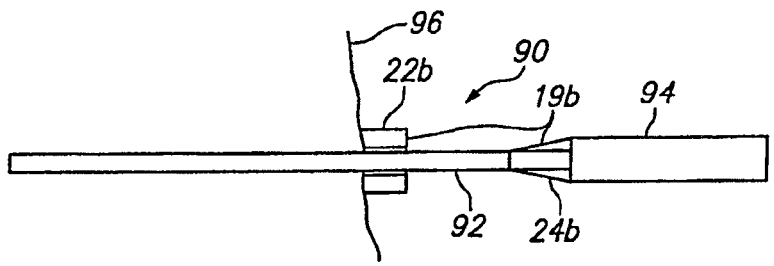
FIG. 22 is a side view of a probe assembly, particularly showing the indexer secured to a skin of a patient.

Each of the indexers 22, 110, 410 described previously is secured to the cannula 12, 102. It should be noted, however, that the indexer 22,110, 410 may also be secured to a patient or other object, such as an operation table or another medical instrument, as long as the indexer 22, 110, 410 is secured in a position relative to which the shaft 14 can move. For example, FIG. 22 shows a probe assembly 90 that is similar to the previously described probe assembly 50, with the exception that it does not use a cannula. Rather, the shaft 92 is directly percutaneously introduced into the body of the patient. In this case, the indexer 22b is secured to the skin 96 of the patient, e.g., by the use of surgical tape, biomaterial adhesive, belt, or stitches. Alternatively, the indexer 22b can be held in position by the physician or assistant. As with the probe assembly 50, the index-key 24b is secured to the shaft 92 or the handle 28. The index-key 24b is adapted to mate with the indexer 22b in a number of positions, as previously described in the probe assembly 50. As such, the probe assembly 90 can be predictably and accurately operated in a number of positions, as discussed previously.

Figure 23:
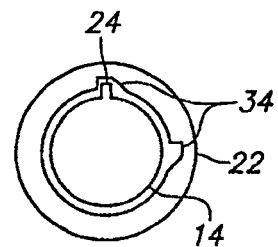
FIG. 23 is a cross sectional view of yet another variation of the angle indexing apparatus.

The indexer 22, 110, 410 and the index-key 24, 108, 408 are not limited to those described previously, and may have other shapes and configurations, so long as the index-key 24, 108, 408 is capable of mating with the indexer 22, 110, 410 in a plurality of positions. For example, as shown in FIG. 23, the keyway 34 of the indexer 22 may have a shape that allows the index-key 24 to be rotated into a second position without requiring changing the longitudinal position of the index-key 24 relative to the indexer 22. Keyway 34 and index-key 24 having other shapes may also be used.

It should also be noted that the operative element 20 is not limited to wires that delivery ablation energy. The operative element 20 can be a variety of instruments such as sensors, cutting devices, mapping instruments, embolic devices, or delivery devices. In addition, while depicted as wires, the operative element 20 can be any type of electrode. Although the indexer 22, 110, 410 and the index-key 24, 108, 408 were discussed previously with reference to a probe assembly or other medical devices, it is intended that the indexer 22, 110, 410 and the index-key 24, 108, 408 can also be fabricated separately from, for subsequent incorporation into, an existing medical device.

It should be noted that the configurations and shapes of the index-key and the indexer should not be limited to the examples discussed previously, and that the index-key and the indexer can have different configurations and/or shapes. For example, the index-key can be any structure or device configured to correspond with the indexer, which can also be any structure or device. In addition, instead of having the index-key coupled to a medical device, in other embodiments, the indexer could be coupled to the medical device. As such, the terms "index-key" and "indexer" should not be limited by the structure to which they are coupled to.

Thus, although several embodiments have been shown and described, it will be apparent to those skilled in the art that many modifications and changes may be made thereunto without the departing from the scope of the invention, which is defined by the following claims.

What is claimed:

1. An apparatus for positioning an energy delivery probe in body tissue, wherein the energy delivery probe comprises a shaft and an operative element coupled to a distal end of the shaft, the apparatus comprising:
    an introducer having a lumen through which the energy delivery probe may be positioned in body tissue;
    a conical index-key comprising a sleeve having a bore configured for being coaxially secured to the shaft of the energy delivery probe, the index-key having a plurality of radically extending key elements; and
    an indexer coupled to a proximal end of the introducer, the indexer having an exterior surface, an interior surface defined by a central bore, a wall thickness defined between the exterior surface and the interior surface, and a plurality of keyways extending from the interior surface towards the exterior surface and located on a respective plurality of radial lines,
    wherein (a) the keyways extend only partially through the wall thickness of the indexer, (b) The keyways are adapted to mate with the plurality of radically extending key elements of the index-key when the index-key is advanced distally relative to the indexer, (c) the plurality of radially extending key elements fit within the keyways of the indexer in at least two positions, and (d) the index-key is rotatable when axially translated away from the indexer.

2. The apparatus of claim 1, wherein the indexer comprises at least four keyways and the plurality of radially extending key elements comprises at least two radially extending key elements.

3. The apparatus of claim 1, wherein the indexer is disposed around the periphery of the introducer.

4. The apparatus of claim 1, further comprising a disk secured to a proximal end of the sleeve.

5. The apparatus of claim 4, wherein the disk secured to the proximal end of the sleeve is configured for being secured to a distal face of a handle on a proximal end of the energy delivery probe.

6. The apparatus of claim 1, wherein the plurality of radially extending key elements comprise fins.

7. The apparatus of claim 1, wherein the plurality of radially extending key elements comprise pins.

8. The apparatus of claim 1, wherein the plurality of radially extending key elements comprise pegs.

9. The apparatus of claim 1, wherein the index-key is configured for being attached to a handle disposed on a proximal end of the energy delivery probe.

10. The apparatus of claim 1, wherein the index-key comprises a distal end and a proximal end, and wherein each of the plurality of key elements extends longitudinally between the distal end and the proximal end of the index-key.

* * * * *